United States Patent
Chu et al.

(10) Patent No.: US 11,471,824 B2
(45) Date of Patent: Oct. 18, 2022

(54) TRANSITION METAL CONTAINING CARBON MOLECULAR SIEVE MEMBRANES AND METHOD TO MAKE THEM

(71) Applicants: Dow Global Technologies LLC, Midland, MI (US); Georgia Tech Research Corporation, Atlanta, GA (US)

(72) Inventors: Yu-Han Chu, Atlanta, GA (US); William J. Koros, Atlanta, GA (US); Liren Xu, Pearland, TX (US); Mark K. Brayden, Baton Rouge, LA (US); Marcos V. Martinez, Rosharon, TX (US)

(73) Assignees: Dow Global Technologies LLC, Midland, MI (US); Georgia Tech Research Corporation, Atlanta, GA (US)

( * ) Notice: Subject to any disclaimer, the term of this patent is extended or adjusted under 35 U.S.C. 154(b) by 228 days.

(21) Appl. No.: 16/096,928

(22) PCT Filed: Apr. 25, 2017

(86) PCT No.: PCT/US2017/029325
§ 371 (c)(1),
(2) Date: Oct. 26, 2018

(87) PCT Pub. No.: WO2017/189522
PCT Pub. Date: Nov. 2, 2017

(65) Prior Publication Data
US 2019/0118133 A1    Apr. 25, 2019

Related U.S. Application Data

(60) Provisional application No. 62/329,245, filed on Apr. 29, 2016.

(51) Int. Cl.
*B01D 53/22* (2006.01)
*B01D 67/00* (2006.01)
(Continued)

(52) U.S. Cl.
CPC ....... *B01D 53/228* (2013.01); *B01D 67/0067* (2013.01); *B01D 69/02* (2013.01);
(Continued)

(58) Field of Classification Search
CPC ..... B01D 53/228; B01D 67/00; B01D 69/145
See application file for complete search history.

(56) References Cited

U.S. PATENT DOCUMENTS 5,234,471 A * 8/1993 Weinberg ........... C08G 73/1039
95/47
5,288,304 A    2/1994 Koros et al.
(Continued)

FOREIGN PATENT DOCUMENTS

| CN | 104998553 A | 10/2015 |
| EP | 459623 B1 | 6/1994 |
| JP | 2007196185 A | 8/2007 |

OTHER PUBLICATIONS

Yoda et al. (Preparation of a platinum and palladium/polyimide nanocomposite film as a precursor of metal-doped carbon molecular sieve membrane via supercritical impregnation, 2004, Chem. Mater. vol. 16, pp. 2363-2368) (Year: 2004).*

(Continued)

*Primary Examiner* — Youngsul Jeong
(74) *Attorney, Agent, or Firm* — Dinsmore & Shohl LLP

(57) ABSTRACT

A carbon molecular sieve (CMS) membrane having improved separation characteristics for separating olefins from their corresponding paraffins is comprised of carbon with at most trace amounts of sulfur and a transition metal, wherein the transition metal is one or more of a group 4-10

(Continued)

and 12 transition metal. The CMS membrane may be made by pyrolyzing a precursor polymer devoid of sulfur in which the precursor polymer has had a transition metal incorporated into it. The pyrolyzing for the precursor having the transition metal incorporated into it is performed in a nonoxidizing atmosphere and at a heating rate and temperature such that the metal has a valence greater than zero (i.e., not metal bonded) to a valence desirably closer to its maximum valence.

19 Claims, 1 Drawing Sheet

(51) Int. Cl.
    *B01D 69/14* (2006.01)
    *B01D 71/02* (2006.01)
    *B01D 69/08* (2006.01)
    *B01D 69/02* (2006.01)
    *C07C 7/144* (2006.01)

(52) U.S. Cl.
    CPC ........... *B01D 69/08* (2013.01); *B01D 69/142* (2013.01); *B01D 69/145* (2013.01); *B01D 71/021* (2013.01); *B01D 71/022* (2013.01); *B01D 2257/102* (2013.01); *B01D 2257/104* (2013.01); *B01D 2257/504* (2013.01); *B01D 2257/7025* (2013.01); *B01D 2325/20* (2013.01); *C07C 7/144* (2013.01); *Y02C 20/20* (2013.01)

(56) References Cited

U.S. PATENT DOCUMENTS

| | | | |
|---|---|---|---|
| 6,471,745 B1 | 10/2002 | Foley et al. | |
| 6,562,110 B2 * | 5/2003 | Koros | B01D 53/228 502/180 |
| 6,565,631 B2 | 5/2003 | Koros et al. | |
| 7,947,114 B2 * | 5/2011 | Hagg | C01B 3/503 95/51 |
| 8,486,179 B2 | 7/2013 | Kiyono et al. | |
| 8,709,133 B2 | 4/2014 | Kiyono et al. | |
| 9,527,045 B2 * | 12/2016 | Koros | B01D 69/06 |
| 2015/0053079 A1 | 2/2015 | Koros et al. | |
| 2015/0182921 A1 | 7/2015 | Koros et al. | |

OTHER PUBLICATIONS

Koresh, J.E. et. al., Molecular sieve permselective membrane, Part I. Presentation of a new device for gas mixture separation, Separation Science and Technology, 1983, p. 8, v.18.

Steel, K.M. et. al., Investigation of Porosity of Carbon Materials and Related Effects on Gas Separation Properties, Carbon, 41, 253, 2003, p. 253.

Suda, H. et. al., Gas Permeation Through Micropores of Carbon Molecular Sieve Membranes Derived From Kapton Polyimide, J. Phys. Chem. B., 1997, p. 3988-3994, v.101.

Geiszler, V. C., et. al., "Effects of Polyimide Pyrolysis Conditions on Carbon Molecular Sieve Membrane Properties," American Chemical Society, 1996, p. 2999-3003, v. 35, No. 9.

Barsema, J.N. et. al., "Functionalized Carbon Molecular Sieve membranes containing Ag-nanoclusters," Journal of Membrane Science, 2003, p. 47-57, v.219.

Teixeria, M. et. al., "Carbon-Al2-O3-Ag composite molecular sieve membranes for gas separation," Chemical Engineering Research and Design, 2012, p. 2338-2345, v.90.

Bloch, E.D., et. al., "Selective Binding of O2 over N2 in a Redox—Active Metal—Organic Framework with Open Iron (II) Coordination Sites," Journal of the American Chemical Society, 2011, p. 14814-14822, v.133.

Barsema, J.N., et. al., "Ag-Functionalized Carbon Molecular-Sieve Membranes Based on Polyelectrolyte/Polyimide Blend Precursors," Advanced Functional Materials, 2005, p. 69-75, v.15, No. 1.

Yoda, S. et. al., Preparation of a platinum and palladium/polyimide nanocomposite film as a precursor of metal-doped carbon molecular sieve membrane via supercritical impregnation, American Chemical Society US, 2004, p. 2363-2368, v.16.

Yoshimune, M. et. al., Gas transport properties of carbon molecular sieve membranes derived from metal containing sulfonated poly(phenylene oxide), Desalination, 2006, p. 66-72, v.193, No. 1-3, Amsterdam, NL.

Suda, H. et. al., Gas permeation properties of carbon molecular sieve membranes dispersed with palladium nano particles via supercritical CO2 impregnation, Desalination, 2006, p. 211-214, v. 193.

Xu, et.al, Olefins-selective asymmetric carbon molecular sieve hollow fiber membranes for hybrid membrane-distillation processes for olefin/paraffin separations, Journal of Membrane Science, 2012, p. 314-323, v. 423-424.

Kim, Y., et. al., "Carbon molecular sieve membranes derived from metal-substituted sulfonated polyimide and their gas separation properties," Journal of Membrane Science, 2003, p. 145-158, v. 226.

Geier, et. al., Selective adsorption of ethylene over ethane and propylene over propane in the metal-organic frameworks M2(dobdc) (M = Mg, Mn, Fe, Co, Ni, Zn, Chemical Science, 2013, p. 2054-2061, v.4.

Pozun, et. al., Why Silver Nanoparticles Are Effective for Olefin Paraffin Separations, The Journal of Physical Chemistry C, 2011, p. 1811-1818, v. 115.

Rose, H.J., "Percentages of Ash, Total Sulfur and Sulfur Forms in U.S.A. Coals," Bituminous Coal Research, Inc., 1958, p. 157-215, Pittsburgh, Pennsylvania.

Merkel, T.C., et. al., "Silver salt facilitated transport membranes for olefin/paraffin separations: Carrier instability and a novel regeneration method," Journal of Membrane Science, 2013, p. 177-189, v. 447.

Ferraz, H.C., et. al., "Recent Achievements in Facilitated Transport Membranes for Separation Processes," Brazilian Journal of Chemical Engineering, 2007, p. 101-118, v. 24, No. 01.

Guo, H., et. al., "Sulfur removal and release behaviors of sulfur-containing model compounds during pyrolysis under intert atmosphere by TG-MS connected with Py-GC," Journal of Fuel Chemistry and Technology, 2014, p. 1160-1166, v. 42, i. 10.

Bloch, E.D., et. al., "Hydrocarbon Separations in a Metal-Organic Framework with Open Iron (II) Coordination Sites," Science, 2012, p. 1606-1610, v.335.

Office Action pertaining to corresponding Japanese Patent Application No. 2018-552754, dated Mar. 30, 2021.

European Communication pursuant to Article 94(3) EPC issued by the European Patent Office for European Patent Application No. 17722273.4 dated May 10, 2022 (7 total pages).

* cited by examiner

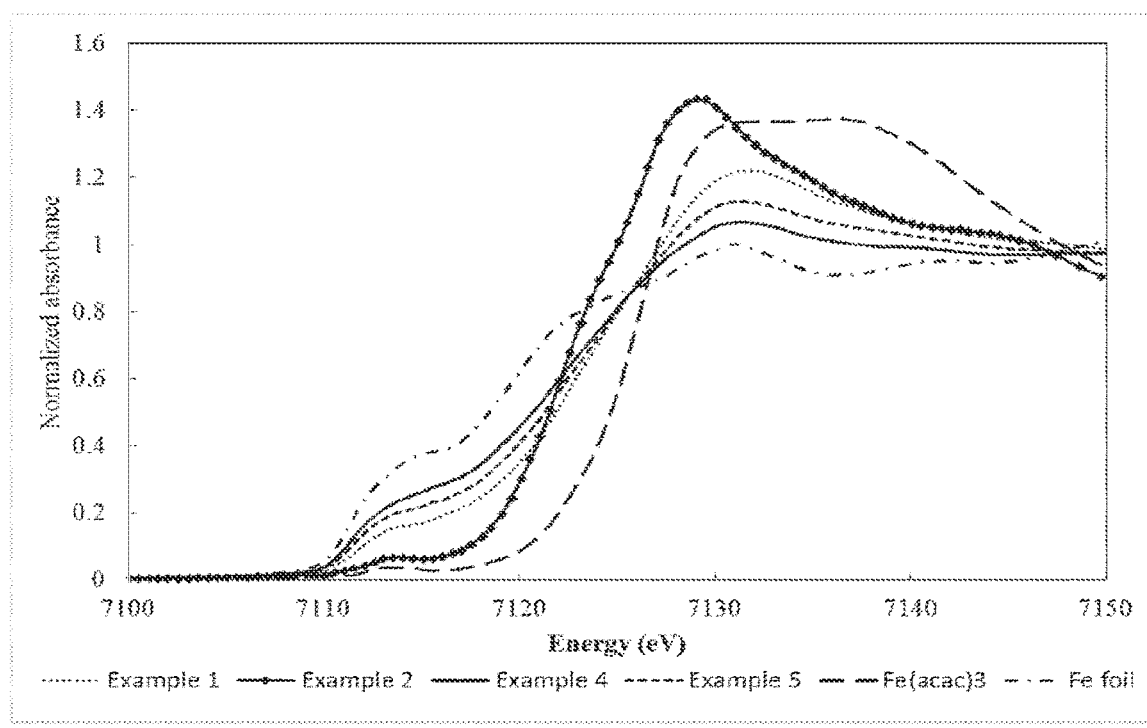

TRANSITION METAL CONTAINING CARBON MOLECULAR SIEVE MEMBRANES AND METHOD TO MAKE THEM

FIELD OF THE INVENTION

The invention relates to carbon molecular sieve (CMS) membranes for use in gas separation. In particular the invention relates to a method for producing CMS membranes with improved selectivity, permeability and stability.

BACKGROUND OF THE INVENTION

Membranes are widely used for the separation of gases and liquids, including for example, separating acid gases, such as $CO_2$ and $H_2S$ from natural gas, and the removal of $O_2$ from air. Gas transport through such membranes is commonly modeled by the sorption-diffusion mechanism. Polymeric membranes have been well studied and are widely available for gaseous separations due to easy process-ability and low cost. CMS membranes, however, have been shown to have attractive separation performance properties exceeding that of polymeric membranes.

CMS membranes are typically produced through thermal pyrolysis of polymer precursors. For example, it is known that defect-free hollow fiber CMS membranes can be produced by pyrolyzing cellulose hollow fibers (J. E. Koresh and A. Soffer, Molecular sieve permselective membrane. Part I. Presentation of a new device for gas mixture separation. Separation Science and Technology, 18, 8 (1983)). In addition, many other polymers have been used to produce CMS membranes in fiber and dense film form, among which polyimides have been favored. Polyimides have a high glass transition temperature, are easy to process, and have one of the highest separation performance among other polymeric membranes, even prior to pyrolysis.

Polyimide hollow fibers have been pyrolyzed to form CMS membranes under vacuum such as described by U.S. Pat. No. 6,565,631. U.S. Pat. No. 6,565,631 also discloses a method of using CMS membranes to separate $CO_2$ from a methane stream containing 10% $CO_2$, at 1000 psia and 50° C., with a selectivity of approximately 45, a selectivity that is much higher than typical commercial polymeric membranes. Other patents that describe processes for producing carbon membranes (both asymmetric hollow "filamentary" and flat sheets), and applications for gas separation, include, for example, U.S. Pat. No. 5,288,304, and EP Patent No. 0459623.

To improve the separation properties of CMS membranes formed from polyimides research has focused primarily on a particular polyimide used and the conditions used to carbonize the particular polyimide. For example, Steel and Koros performed a detailed investigation of the impact of pyrolysis temperature, thermal soak time, and polymer composition on the performance of carbon membranes. (K. M. Steel and W. J. Koros, Investigation of Porosity of Carbon Materials and Related Effects on Gas Separation Properties, Carbon, 41, 253 (2003).) Membranes were produced in an air atmosphere at 0.05 mm Hg pressure. The results showed that increases in both temperature and thermal soak time increased the selectivity but decreased permeance for $CO_2$/$CH_4$ separation. In addition, Steel et al showed that a precursor polymer with a tightly packed structure tends to lead to a CMS membrane having higher selectivity compared with less compact precursor polymers.

The impact of pyrolysis atmosphere has been researched only to a limited extent. Suda and Haraya disclosed the formation of CMS membranes under different environments. (H. Suda and K. Haraya, Gas Permeation Through Micropores of Carbon Molecular Sieve Membranes Derived From Kapton Polyimide, J. Phys. Chem. B, 101, 3988 (1997).) CMS dense films were prepared from polyimide Kapton® at 1000° C. in either argon or in vacuum. According to their gas separation properties, the results of an $O_2/N_2$ separation were almost the same between 6 membranes formed under the different atmospheres. Suda and Haraya did not disclose the effects of atmosphere on $CO_2$ separation from natural gas, nor disclose how separation properties vary with ability and low cost. Similarly, Geiszler and Koros disclosed the results of CMS fibers produced from pyrolysis of fluorinated polyimide in helium and argon for both $O_2/N_2$ and $H_2/N_2$ separations. (V. C. GEISZLER and W. J. Koros, "Effects of Polyimide Pyrolysis Conditions on Carbon Molecular Sieve Membrane Properties," American Chemical Society, 1996, v. 35, no. 9, pp. 2999-3003). That paper disclosed a slightly higher selectivity with vacuum pyrolysis than the purged pyrolysis processes. In addition, Geiszler and Koros showed that the flow rate of the purge gases impacted performance. In U.S. Pat. No. 8,486,179, the effect of using atmospheres having small amounts of oxygen in the pyrolysis atmosphere was described.

Limited research has been done on changing the chemistry of the polyimide such as incorporating metals that may have an affinity for particular gas molecules of interest (e.g., ethylene and propylene). Filler particles (clusters) of silver particles have been mixed in carbon membranes formed from P84 3,3'-4,4'-Benzophenone tetracarboxylic dianhydride (BTDA)-toluene diisocyanate/methylene diisocyanate (BTDA-TDI/MDI) copolyimide to separate He, $CO_2$, $O_2$ and $N_2$, has been described by J. N. Barsema et al., in *J. Mem. Sci.* 219 (2003) 47-57. Filler particles of alumina and silver were loaded into a carbonized phenolic resin for separating $C_3H_6$, $C_3H_8$, H, He, $N_2$, $CO_2$ and $O_2$ as described by M. Teixeira et al., Chem Eng. Res. Des. 90 (2012) 2338-2345. Particular metals such as silver and copper have been incorporated into sulfonated polymers such as sulfonated poly(phenylene oxide) in which metals were formed upon carbonization of the sulfonated polymer to separate H, He, $N_2$, $CO_2$ and $O_2$, but the residual sulfur may be potentially poisonous as described by M. Yoshimune et al., in *Desalination* 193 (2006) 66-72. Likewise, silver was incorporated into carbonized blends of a P84 copolyimide and a sulfonated poly (ether ether ketone) for the separation of He, $N_2$, $CO_2$ and $O_2$.

It would be desirable to provide a CMS membrane and method to make the CMS membrane to improve the separation of particular gases such as ethane from ethylene and propylene from propane. In particular, it would be desirable to provide such a CMS membrane that avoids one or more of the problems of the prior art such as one described above (e.g., sulfur poisoning).

SUMMARY OF THE INVENTION

A first aspect of the invention is a carbon molecular sieve membrane comprising, carbon with at most trace amounts of sulfur and a transition metal, wherein the transition metal is one or more of a group 4-10 and 12 transition metal. When referring to group of transition metal groups, the group being referred to is IUPAC new notation (periodic table) as per *Handbook of Chemistry and Physics*, 66$^{th}$ Ed., CRC Press Inc. (1985).

A second aspect is a process for separating a gas molecule from a feed gas comprised of the gas molecule and at least one other gas molecule comprising
(i) providing the carbon molecular sieve membrane of the first aspect; and
(ii) flowing the gas feed through and over said carbon molecular sieve membrane to produce a first permeate stream having an increased concentration of the gas molecule and a second retentate stream having a decreased concentration of the gas molecule.

A third aspect of the invention is a method of making a carbon molecular sieve membrane comprising,
(i) providing a precursor polymer without any sulfur;
(ii) incorporating a transition metal into the precursor polymer to form a transition metal bearing precursor polymer,
(iii) heating said transition metal bearing precursor polymer to a final pyrolysis temperature and non-oxidizing atmosphere sufficient to form the carbon molecular sieve membrane containing the transition metal; and
(iv) cooling the carbon molecular sieve membrane to room temperature.

A fourth aspect of the invention is a carbon molecular sieve module comprising a sealable enclosure comprised of: a plurality of carbon molecular sieve membranes, comprising at least one carbon molecular sieve membrane of the first aspect, contained within the sealable enclosure; an inlet for introducing a gas feed comprised of at least two differing gas molecules; a first outlet for permitting egress of a permeate gas stream; and a second outlet for egress of a retentate gas stream.

The gas separation method is particularly useful for separating gas molecules in gas feeds that have very similar molecular sizes such as ethane/ethylene and propane/propylene. It may also be used to separate gases from atmospheric air such as oxygen or separating gases (e.g., methane) in natural gas feeds.

BRIEF DESCRIPTION OF THE DRAWINGS

The FIGURE shows the X-ray absorption near edge structure (XANES) results for the valence state of Fe present in the Examples of the invention and reference materials showing, metallic Fe—Fe bonds and $Fe^{+3}$ valence.

DETAILED DESCRIPTION OF THE INVENTION

The polyimide precursor polymer may be any polyimide polymer useful for making CMS membranes that does not contain sulfur and in which a transition metal may be added. In one embodiment, the polyimide contains moieties (e.g., polar moieties such as 3,5-diaminobenzoic acid (DABA) and 5,5'-Methylene-bis(anthranilic acid) (MBAA)) that allow for the incorporation of the transition metal into the polyimide structure ionically. The polyimide may be a conventional or fluorinated polyimide. Desirable polyimides typically contain at least two different moieties selected from 2,4,6-trimethyl-1,3-phenylene diamine (DAM), oxydianaline (ODA), dimethyl-3,7-diaminodiphenyl-thiophene-5,5'-dioxide (DDBT), 3,5-diaminobenzoic acid (DABA), 2.3, 5,6-tetramethyl-1,4-phenylene diamine (durene), meta-phenylenediamine (m-PDA), 2,4-diaminotolune (2,4-DAT), tetramethylmethylenedianaline (TMMDA), 5,5'-[2,2,2-trifluoro-1-(trifluoro-methyl)ethylidene]-1,3-isobenzofuran-dion (6FDA), 3,3',4,4'-biphenyl tetracarboxylic dianhydride (BPDA), pyromellitic dianhydride (PMDA), 1,4,5,8-naphthalene tetracarboxylic dianhydride (NTDA), and benzophenone tetracarboxylic dianhydride (BTDA), with two or more of 6FDA, BPDA and DAM being preferred.

An exemplary polyimide, designated as 6FDA/BPDA-DAM, may be synthesized via thermal or chemical processes from a combination of three monomers: DAM; 6FDA, and BPDA, each commercially available for example from Sigma-Aldrich Corporation. Formula 1 below shows a representative structure for 6FDA/BPDA-DAM, with a potential for adjusting the ratio between X and Y to tune polymer properties. As used in examples below, a 1:1 ratio of component X and component Y may also abbreviated as 6FDA/BPDA(1:1)-DAM.

Formula 1

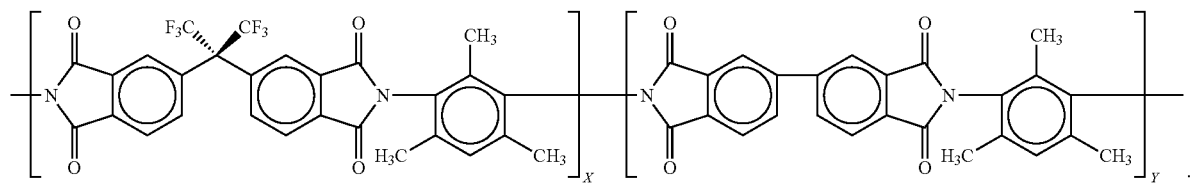

Chemical structure of 6FDA/BPDA-DAM

Another exemplary polyimide, designated as 6FDA-DAM lacks BPDA such that Y equals zero in Formula 1 above. Formula 2 below shows a representative structure for this polyimide.

Formula 2

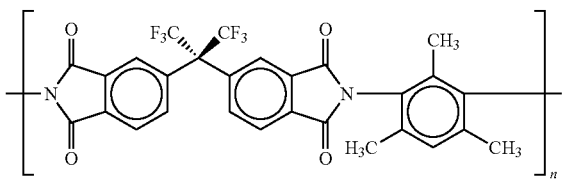

Chemical structure of 6FDA-DAM

A particularly useful polyimide for ionically incorporating a transition metal is 4,4'-hexafluoroisopropylidene diphthalic anhydride (6FDA),2,4,6-trimethyl-1,3-phenylenediamine (DAM) and 3,5-diaminobenzoic acid (DABA) as shown below in Formula 3, and which may be abbreviated as 6FDA-DAM:DABA (3:2):

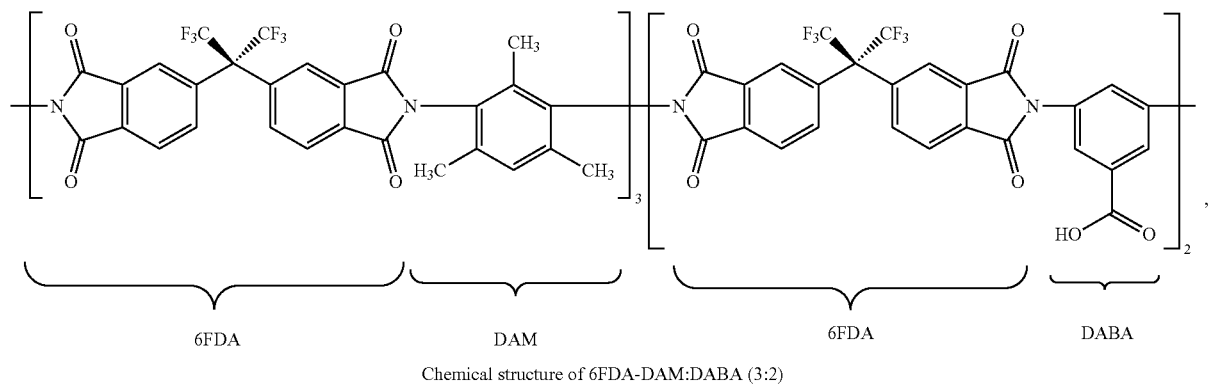

Chemical structure of 6FDA-DAM:DABA (3:2)

To realize a CMS membrane of the invention, a transition metal is incorporated into the precursor polymer to form a transition metal bearing precursor polymer. The incorporation may be by any useful method whereby the transition metal may be incorporated into the polyimide. It is desirable that the transition metal is incorporated in the polyimide on a fine scale. The transition metal may be incorporated by physical mixing or blending. For example, the polymer and a transition metal salt may be dissolved in a solvent, mixed and the solvent removed. In a particular embodiment a transition metal salt and a polyimide precursor having polar moieties are dissolved in a solvent and upon removal of the solvent with or without further heating, the salt decomposes and the transition metal ionically cross-links the polyimide polymer through the polar moieties. An example of such incorporation is illustrated as follows:

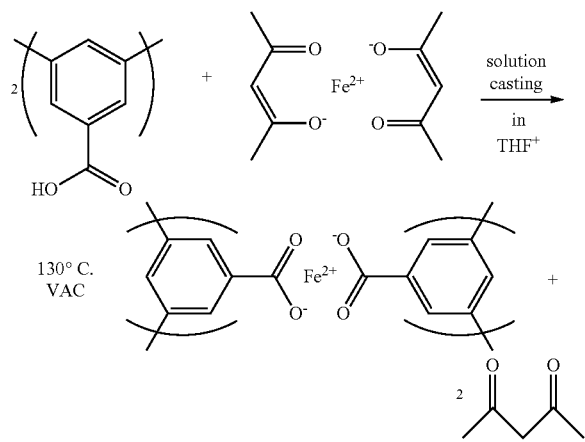

Transition metals may also be incorporated during the polyimide synthesis process. For example, a transition metal salt is added to a solution of polyamic acid having polar moieties, and the mixture is cast into a film. As the film is thermally cured at high temperature, the polyamic acid converts to polyimide and the metal ions react with the polar moieties to form an ionomer.

Incorporating the transition metal may also be achieved by infusing. For example, the metal may be incorporated into a solid polymer precursor by infusing a metal compound dissolved in a solvent (e.g., water, ethanol, methanol, hexane, $HCF_3$, and supercritical $CO_2$). An example of a metal compound useful to infuse or incorporate during the synthesis of the polyimide, other than those previously mentioned, is a metallocene such as ferrocene.

The transition metal salt may be any salt useful for incorporating into the polyimide, but typically is an organic salt such as a transition metal acetylacetonate, metal acetate, or metal chloride. Mixtures of differing salts as well as differing transition metals may be used.

The transition metal is a group 4-10 and 12 transition metal in which the meaning of "group" was defined above. Preferably, the transition metal is a group 4-10 transition metal. Desirably, the transition metal is V, Cr, Mn, Fe, Co Ni, Zn, Ru, Rh, Pd, W, Re, Os, Pt, Au or combination thereof. In a particular embodiment the transition metal is Mn, Fe, Co Ni or combination thereof. More preferably, the transition metal is Fe, Co Ni or combination thereof. In a particular embodiment, the transition metal is present in the CMS membrane at a valence state that is greater than 0 (i.e., not in a metal form), but less than the maximum valence state as determined by X-ray absorption near edge structure (XANES). Illustratively, the average valence state of Fe is greater than 0 and less than 3 as determined by XANES.

The amount of transition metal in the CMS membrane may be any amount useful to enhance the combination of permeance and selectivity of the desired gas molecule to be separated (e.g., ethylene or propylene). Generally, the amount of the transition metal is from 0.01% to 15% by weight of the CMS membrane. Desirably, the amount of transition metal is at least about 0.1%, 0.5%, or 1% to 12%, 10% or 8% by weight of the CMS membrane.

In forming the CMS membranes, the polyimides incorporating the transition metal are formed into hollow fiber membranes or film membranes. These as formed membranes (i.e., not yet pyrolyzed) are substantially defect-free. "Defect-free" means that selectivity of a gas pair, typically oxygen ($O_2$) and nitrogen ($N_2$), through a hollow fiber membrane or film membrane is at least 90 percent of the selectivity for the same gas pair through a dense film prepared from the same composition as that used to make the polymeric precursor hollow fiber membrane. By way of illustration, a 6FDA/BPDA(1:1)-DAM polymer has an intrinsic $O_2/N_2$ selectivity (also known as "dense film selectivity") of 4.1.

Conventional procedures to make the polyimide hollow fibers or films may be used. For example, coextrusion procedures including such as a dry-jet wet spinning process (in which an air gap exists between the tip of the spinneret and the coagulation or quench bath) or a wet spinning process (with zero air-gap distance) may be used to make the hollow fibers and solution casting may be used to make the films.

The particular heating rates, final pyrolysis temperatures, cooling rates and combinations of them are somewhat dependent on the particular polyimide, transition metal used and desired separations to be performed. Nevertheless, generally, it has been found particularly for separating olefins (e.g., ethylene and propylene) from their paraffin analogs, that it is desirable to heat to the maximum pyrolysis temperature and hold at that temperature such that the transition metal tends to have an average valence state closer to its maximum as given in the periodic table in the *Handbook of Chemistry and Physics*, $66^{th}$ Ed., CRC Press Inc. (1985) as determined by XANES. Generally, this tends to mean that is it is desirable to heat rapidly, hold for short times at lower maximum pyrolysis temperatures.

Generally, the maximum or final pyrolysis temperature to carbonize the transition metal containing polyimide may be anywhere from 400 to 1000° C., but preferably is from about 500° C. to 700° C. or 600° C. The heating rate may be any suitable such as 1° C./minute to 100° C./minute, but desirably is from about 5° C./minute or 10° C./minute to 25° C./minute, or 20° C./minute. The amount of time at the final pyrolysis temperature is desirably from as short time practicable in view of the heating rate, e.g., several seconds or one minute to about 60 minutes. In an embodiment, the hold time at the final pyrolysis temperature is from 15 minutes to 60 minutes. Longer times tend not to be necessary and may negatively affect the desired combination of permeance and selectivity. Likewise, the cooling rate may be any suitable method such as merely passively cooling the furnace (by shutting the power off), but it may be desirable to cool rapidly or accelerate the cooling by a heat removal method.

Exemplary heat removal methods include: flowing a gas directly over the carbon molecular sieve membrane within the furnace; flowing a gas through the carbon molecular sieve membrane within the furnace; removing the furnace insulation; flowing a liquid over at least a portion of the furnace or flowing a gas over at least a portion of the furnace. Any one or combination of heat removal methods may be used, with it being desirable to have the cooling rate as high as possible at least from the final pyrolysis temperature to about 400° C. or to room temperature. Generally, the average cooling rate from the final pyrolysis temperature to 400° C. is at least about 2, 4 or 8° C./minute. The average heating rate is the temperature difference between the final pyrolysis temperature and 400° C. and the total time it takes to reach 400° C. The cooling rate from 400° C. to room temperature may be any practicable with faster being desirable merely for productivity sake.

It is understood that all temperatures, heating rates and cooling rates are those as measured in the furnace and not the actual CMS membranes being formed. The actual temperature of the CMS membranes being formed may vary somewhat due to temperature lag due to thermal mass within the furnace, particular furnace used and the like and is readily determinable by one skilled in the art.

Any suitable supporting means for holding the CMS membranes may be used during the pyrolysis including sandwiching between two metallic wire meshes or using a stainless steel mesh plate in combination with stainless steel wires and as described by U.S. Pat. No. 8,709,133 at col. 6, line 58 to col. 7, line 4, which is incorporated by reference. A quartz plate may be desirably used when supporting a dense film as opposed to a hollow fiber.

The transition metal containing polyimide may be carbonized under various inert gas purge or vacuum conditions, preferably under inert gas purge conditions, for the vacuum pyrolysis, preferably at low pressures (e.g. less than 0.1 millibar). In one embodiment the pyrolysis utilizes a controlled purge gas atmosphere during pyrolysis in which low levels of oxygen are present in an inert gas. By way of example, an inert gas such as argon is used as the purge gas atmosphere. Other suitable inert gases include, but are not limited to, nitrogen, helium, or any combinations thereof. By using any suitable method such as a valve, the inert gas containing a specific concentration of oxygen may be introduced into the pyrolysis atmosphere. For example, the amount of oxygen in the purge atmosphere may be less than about 50 ppm (parts per million) $O_2$/Ar. Alternatively, the amount of oxygen in the purge atmosphere may be less than 40 ppm $O_2$/Ar. Embodiments include pyrolysis atmospheres with about 8 ppm, 7 ppm, or 4 ppm $O_2$/Ar.

The gas permeation properties of a membrane can be determined by gas permeation experiments. Two intrinsic properties have utility in evaluating separation performance of a membrane material: its "permeability," a measure of the membrane's intrinsic productivity; and its "selectivity," a measure of the membrane's separation efficiency. One typically determines "permeability" in Barrer (1 Barrer=$10^{-10}$ [$cm^3$ (STP) cm]/[$cm^2$ s cmHg]), calculated as the flux ($n_i$) divided by the partial pressure difference between the membrane upstream and downstream ($\Delta p_i$), and multiplied by the thickness of the membrane (l).

$$P_i = \frac{n_i l}{\Delta p_i}$$

Another term, "permeance," is defined herein as productivity of asymmetric hollow fiber membranes and is typically measured in Gas Permeation Units (GPU) (1 GPU=$10^{-6}$ [$cm^3$ (STP)]/[$cm^2$ s cmHg]), determined by dividing permeability by effective membrane separation layer thickness.

$$\left(\frac{P_i}{l}\right) = \frac{n_i}{\Delta p_i}$$

Finally, "selectivity" is defined herein as the ability of one gas's permeability through the membrane or permeance relative to the same property of another gas. It is measured as a unitless ratio.

$$\infty_{i/j} = \frac{P_i}{P_j} = \frac{\left(\frac{P_i}{l}\right)}{\left(\frac{P_j}{l}\right)}$$

In a particular embodiment, the CMS membrane produced by the method enables a carbon hollow fiber CMS membrane that has a permeance of at least 5 GPU for a target gas molecule (permeate) and a selectivity of at least 10 and a stability such that said permeance and selectivity varies less than 20% after being continuously separating a feed gas comprised of a retentate gas molecule and permeate gas molecule for 10 days. Desirably, the permeance and selectivity varies less than 15%, 10% or 5% after continuously separating a feed gas comprised of a retentate and permeate gas molecule pair for 10, 30 or 60 days. In particular embodiments the permeate/retentate gas molecule pairs may be ethylene/ethane, propylene/propane, butylene/butane, methane/carbon dioxide, methane/water, oxygen/nitrogen, and methane/hydrogen sulfide. Illustratively, the feed gas generally is comprised of at least 50% the permeate gas molecule (e.g., ethylene or propylene) and 25% of retentate gas molecule (e.g., ethane or propane).

In a particular embodiment the CMS membrane produced has a permeance of at least 10 GPU for propylene (permeate) and a selectivity of at least 35 propylene/propane. Desirably, in this embodiment the permeance is at least 12, 15 or even 18 GPU for propylene. Likewise, in this embodiment the selectivity is at least 40, 45 or even 50 for propylene/propane. In another particular embodiment, the CMS membrane produced has a permeance of at least 10 GPU for ethylene (permeate) and a selectivity of at least 6 ethylene/ethane. Desirably, in this embodiment the permeance is at least 15, 18 or even 20 GPU for ethylene. Likewise, in this embodiment the selectivity is at least 8, 10 or even 12 for ethylene/ethane. In a further embodiment, the CMS membrane produced has a permeance of at least 10 GPU for butylene (permeate) and a selectivity of at least 5 for butylene/butane. Desirably, in this embodiment the permeance is at least 20, 30 or even 40 GPU for butylene. Likewise, in this embodiment the selectivity is at least 10, 15 or even 30 for butylene/butane.

The CMS membranes are particularly suitable for separating gases that are similar in sizes such as described above and involve flowing a gas feed containing a desired gas molecule and at least one other gas molecule through the CMS membrane. The flowing results in a first stream have an increased concentration of the desired gas molecule and second stream having an increased concentration of the other gas molecule. The process may be utilized to separate any of the aforementioned gas pairs and in particular is suitable for separating ethylene and ethane or propylene and propylene. Likewise, the process exhibits the same stability as it relates to permeance and selectivity over time as described above. When practicing the process, the CMS membrane is desirably fabricated into a module comprising a sealable enclosure comprised of a plurality of carbon molecular sieve membranes that is comprised of at least one carbon molecular sieve membrane produced by the method of the invention that are contained within the sealable enclosure. The sealable enclosure having an inlet for introducing a gas feed comprised of at least two differing gas molecules; a first outlet for permitting egress of a permeate gas stream; and a second outlet for egress of a retentate gas stream.

EXAMPLES

Examples 1-5

The CMS membranes were made using 6FDA-DAM:DABA (3:2) polymer. The 6FDA-DAM:DABA was acquired from Akron Polymer Systems, Inc., Akron, Ohio. The polymer was dried under vacuum at 110° C. overnight to remove moisture. The dried polymer was dissolved in tetrahydrofuran (THF) in a 40 ml vial (vial A) to form a 2 to 3 wt % polymer solution. Iron(II) acetylacetonate (Sigma-Aldrich, St. Louis, Mo.) was dissolved in THF in a 20 ml vial (vial B) to form a Fe-containing solution. The two solutions were filtered with 0.20 micron PTFE filters respectively, and the Fe-containing solution in vial B was added to vial A to form the Fe-containing polymer dope for casting. The compositions of the solutions are shown in Table 1.

TABLE 1

| Casting Solution Formulation | | |
| --- | --- | --- |
| | Solvent | Solute |
| Vial A | 20 ml THF | 0.5 g polymer |
| Vial B | 5 ml THF | 0.05 g iron(II) acetylacetonate |

Dense films were prepared by casting the mixed solution into a Teflon casting dish inside a glove bag at room temperature to allow for a slow evaporation rate. After at least 3 days, the vitrified films were removed from the bag and dried in a vacuum oven at 130° C. for 24 hours to remove residual solvent. The dried films having a thickness of about 80 micron were then cut into 0.75 inch diameter discs that were then pyrolyzed as described below.

The discs were pyrolyzed to form the CMS membranes by placing the discs on a slotted quartz plate with spacing between each disc. The combination of the discs and quartz plate were placed into a quartz tube of a tube furnace. The films were pyrolyzed under an inert gas (argon flowing at a rate of 200 standard cubic centimeters per minute (sccm)). Prior to pyrolyzing the furnace was purged with inert gas to remove oxygen for a minimum of ten hours to reduce the oxygen level to less than 1 ppm. The films were heated at a ramp rate and held at the maximum soak temperature as shown in Table 2 to form the final CMS membranes. The formed CMS membranes were all cooled passively (furnace shut off with the same inert gas flow maintained until the furnace was cooled to about room temperature, ~4-6 hours.

After cooling, the CMS membranes were masked in a dense film permeation cell by using impermeable aluminum tape and five minute epoxy (3M™ Scotch-Weld™ Epoxy Adhesive DP110). The permeation cell was then placed in a constant-volume permeation system, and the system was stabilized at 35° C. For each permeation test, the entire system was evacuated for 18 hours. After evacuation, the upstream was pressurized with feed gas at about 50 pounds per square inch absolute pressure (psia) while the downstream was kept at vacuum. The pressure rise in a constant, known downstream volume was monitored by a pressure transducer and recorded over time by LabVIEW (National Instruments, Austin, Tex.) until a steady state was achieved.

Examples 1 through 5 were evaluated for multiple-component olefins/paraffins mixture separation. The multicomponent feed contained 54.60 mol % ethylene, 17.00 mol % ethane, 15.10 mol % propylene, and 13.30 mol % propane. The separation characteristics of the CMS membranes of Examples 1 through 5 for the multicomponent feed are shown in Table 3. Example 2 and Comparative Example 1 were also tested for pure gas permeation, and their permeation characteristics and selectivity are shown in Table 4.

A pressure decay sorption system was used to measure sorption properties of CMS membranes. The CMS membranes were crushed into small pieces between two pieces of weighing paper and wrapped with aluminum foil securely. The samples were loaded into the sample cell chamber, and the sorption cell was then placed in an oil bath with a heating circulator to maintain uniform temperature at 35° C. The entire system was evacuated for 18 hours before testing. For the measurement at each pressure level, the reservoir cell chamber was filled with feed gas and equilibrated for 20 to 25 minutes. The valve between the reservoir and the sample cell was then opened carefully to introduce gas into the sample cell. The pressure in both the reservoir and sample cell was monitored by a pressure transducer and recorded over time by LabVIEW (National Instruments, Austin, Tex.) until the pressure became constant. The amount of sorbed gas was calculated based on a mole balance. Gas uptake was plotted against equilibrium pressure and the data was fitted using a Langmuir model to obtain sorption isotherms. The sorption results of ethane and ethylene are shown in Table 2.

For CMS membranes of Examples 1,2, 4 and 5 as well as for the iron foil and iron acetylacetonate, X-ray absorption near edge structure (XANES) was performed to determine the valence state of the Fe, with the Fe foil representing a zero or metallic Fe—Fe bond and the iron acetylacetonate representing an $Fe^{+3}$ valence. The Fe K-edge XANES spectra were collected at Argonne National Laboratory, Lemont, Ill. in transmission mode at room temperature. The results are shown in the FIGURE, where it can be seen that the faster lower temperature pyrolysis conditions results in an average Fe bonding state that is closer to $Fe^{+3}$.

Comparative Examples 1 and 2

Comparative Example CMS membranes 1 and 2 were prepared and tested in the same manner as Examples 1 through 5, except that the casting solution did not contain the iron(II) acetylacetonate. The particular heating conditions to form these CMS membranes are shown in Table 2. The separation characteristics of these CMS membranes for the multicomponent feed are shown in Table 3. Comparative Example 2 was also tested for pure gas permeation, and its separation characteristics are shown in Table 4.

The results in Table 2 show that metal-containing CMS membranes (i.e., Examples 2 and 3) pyrolyzed with a lower temperature and at a faster heating rate show $C_2H_4/C_2H_6$ sorption selectivity that is enhanced compared to CMS membranes pyrolyzed at a higher temperature and slower heating rate (Comparative Examples 1, 4 and 5). The sorption data also show that Examples 2 and 3 have improved sorption selectivity compared to membranes without iron (Comparative Examples 1 and 2).

The separation characteristics for the multicomponent feed in Table 3 also show that Examples 2, 3 and 5 each have a $C_2H_4/C_2H_6$ selectivity that is much higher than the $C_2H_4/C_2H_6$ selectivity of Comparative Examples 1 and 2. Likewise the pure gas permeation characteristics shown in Table 4 show that the metal-containing CMS membrane (Example 2) has a much higher $C_2H_4/C_2H_6$ selectivity of 9.4 than Comparative 2's $C_2H_4/C_2H_6$ selectivity of 2.9 in which both were made using the same heating rate and temperature. From XANES results shown in the FIGURE, iron in the metal-containing CMS membranes of the Examples have a higher valence state ($Fe^{2+}$, $Fe^{3+}$, or between $Fe^{2+}$ and $Fe^{3+}$) when the films are pyrolyzed at a lower temperature and at a faster heating rate. That is, Examples 2 and 3 have the most desirable permeation and separation characteristics, which correspond to a higher iron valence state as compared to Examples 1, 4 and 5.

TABLE 2

| | Pyrolysis Conditions | | | | |
|---|---|---|---|---|---|
| Example | Temp (° C.) | Atmosphere (sccm/Ar) | Heating Rate (C./min) | Soak Time (min) | Sorption Selectivity ($C_2H_4/C_2H_6$) * |
| 1 | 550 | 200 | 3.85 | 120 | 1.02 |
| 2 | 550 | 200 | 10 | 0 | 1.19 |
| 3 | 550 | 200 | 15 | 0 | 1.13 |
| 4 | 675 | 200 | 3.85 | 120 | 0.98 |
| 5 | 675 | 200 | 10 | 0 | 1.06 |
| Comp. 1 | 550 | 200 | 10 | 0 | 1.00 |
| Comp. 2 | 675 | 200 | 10 | 0 | 1.08 |

\* = @ 50 psi

TABLE 3

| Example | C2"/C2 | C2"/C3 | C3"/C2 | C2"/C3" | C2" (Barrer) | C2 (Barrer) | C3" (Barrer) | C3 (Barrer) |
|---|---|---|---|---|---|---|---|---|
| 1 | 4.95 | — | 3.50 | 1.42 | 111.69 | 22.72 | 80.91 | — |
| 2 | 8.53 ± 0.47 | ND | 1.88 ± 0.18 | 4.61 ± 0.68 | 95.15 ± 30.56 | 11.64 ± 4.17 | 22.45 ± 9.06 | ND |
| 3 | 9.53 | ND | 1.86 | 5.12 | 45.04 | 4.76 | 9.02 | ND |
| 4 | ND | ND | ND | ND | ND | ND | ND | ND |
| 5 | 7.40 | ND | 2.93 | 2.52 | 37.37 | 5.08 | 15.18 | ND |
| Comp. 1 | 3.30 ± 0.39 | 23.15 ± 6.38 | 3.05 ± 0.15 | 1.09 ± 0.18 | 1159.30 ± 100.71 | 354.65 ± 11.08 | 1101.46 ± 88.32 | 54.51 ± 10.57 |
| Comp. 2 | 4.75 | 143.90 | 2.98 | 1.60 | 297.84 | 63.06 | 191.01 | 2.26 |

C2" = ethylene;
C2 = ethane;
C3" = propylene;
C3 = propane.
—: unavailable due to the test limitation of gas chromatography (GC)
ND = Not determined.

TABLE 4

| Example | C2"/C2 | C2" (Barrer) | C2 (Barrer) |
|---|---|---|---|
| 2 | 9.35 | 63.17 | 6.76 |
| Comp. 1 | 2.89 | 1244.5 | 431.06 |

C2" = ethylene;
C2 = ethane;

What is claimed is:
1. A carbon molecular sieve (CMS) membrane comprising, polyimide polymer, a transition metal and in the absence of sulfur, wherein the transition metal is V, Cr, Mn, Fe, Co, Ni, Zn, Ru, Rh, Pd, W, Re, Os, Pt, Au or a combination thereof, wherein the transition metal is present in the CMS membrane at a valence state that is greater than 0, but less than the maximum valence state as determined by X-ray absorption near edge structure (XANES), wherein the polyimide polymer comprises 3,5-diaminobenzoic acid (DABA).

2. The carbon molecular sieve membrane of claim 1, wherein the transition metal is a Mn, Fe, Co Ni or combination thereof.

3. The carbon molecular sieve membrane of claim 1, wherein the transition metal is a Fe, Co Ni or combination thereof.

4. The carbon molecular sieve membrane of claim 1, wherein the transition metal is Fe and the valence state is between greater than 0 and 3.

5. The carbon molecular sieve membrane of claim 1, wherein the transition metal is present in an amount of 0.5% to 10% by weight of the carbon molecular sieve membrane.

6. The carbon molecular sieve membrane of claim 1, wherein the transition metal is incorporated by ionic bonding of the transition metal to one or more moieties present in the polyimide polymer.

7. The carbon molecular sieve membrane of claim 1, wherein the transition metal is incorporated by ionic bonding of the transition metal to the diaminobenzoic acid (DABA) moieties in the polyimide polymer.

8. A process for separating a gas molecule from a feed gas comprised of the gas molecule and at least one other gas molecule comprising
   (i) providing the carbon molecular sieve membrane recited in claim 1; and
   (ii) flowing the gas feed through and over said carbon molecular sieve membrane to produce a first permeate stream having an increased concentration of the gas molecule and a second retentate stream having a decreased concentration of the gas molecule.

9. The process of claim 8, wherein the gas molecule and other gas molecule is: ethylene and ethane; propylene and propane; butylene and butane; oxygen and nitrogen; or carbon dioxide and methane.

10. The process of claim 9, wherein ethylene has a selectivity of least 6 of ethylene/ethane and an ethylene permeance of at least 10 Gas Permeation Unit (GPU) at 35° C.

11. The process of claim 9, wherein propylene has a selectivity of least 35 of propylene/propane and a propylene permeance of at least 10 GPU at 35° C.

12. A method of making the carbon molecular sieve membrane recited in claim 1 comprising:

(i) providing a precursor polymer without any sulfur;
(ii) incorporating a transition metal into the precursor polymer to form a transition metal bearing precursor polymer,
(iii) heating said transition metal bearing precursor polymer to a final pyrolysis temperature under a non-oxidizing atmosphere sufficient to form the carbon molecular sieve membrane containing the transition metal wherein the transition metal is present in the CMS membrane at a valence state that is greater than 0, but less than the maximum valence state as determined by X-ray absorption near edge structure (XANES).; and
(iv) cooling the carbon molecular sieve membrane to room temperature.

13. The method of claim 12, wherein the incorporating of the transition metal into the precursor polymer is conducted by ionic bonding of the transition metal to one or more moieties present in the precursor polymer.

14. The method of claim 12, wherein the precursor polymer is a polyimide.

15. The method of claim 14, wherein the precursor polymer is a polyimide copolymer comprised of 3,5-diaminobenzoic acid (DABA).

16. The method of claim 14, wherein the incorporating of the transition metal into the precursor polymer is conducted by ionic bonding of the transition metal to one or more moieties present in the precursor polymer.

17. The method of claim 14, wherein the incorporating of the transition metal into the precursor polymer is conducted by adding the transition metal during synthesis of the polyimide or by infusing the transition metal dissolved in a solvent.

18. The method of claim 15, wherein the incorporating of the transition metal into the precursor polymer is conducted by ionic bonding of the transition metal with the diaminobenzoic acid (DABA) moieties of a copolymer of hexafluoroisopropylidene diphthalic anhydride (6FDA),2,4,6-trimethyl-1,3-phenylenediamine (DAM) and the diaminobenzoic acid (DABA).

19. A carbon molecular sieve module comprising a sealable enclosure comprised of: a plurality of carbon molecular sieve membranes, comprising at least one carbon molecular sieve membrane recited in claim 1, contained within the sealable enclosure; an inlet for introducing a gas feed comprised of at least two differing gas molecules; a first outlet for permitting egress of a permeate gas stream; and a second outlet for egress of a retentate gas stream.

* * * * *